(12) United States Patent
Stewart et al.

(10) Patent No.: US 8,263,639 B2
(45) Date of Patent: Sep. 11, 2012

(54) MULTIFUNCTIONAL METAL-CHELATING LIGANDS

(75) Inventors: Michael Stewart, Washington, DC (US); Kimihiro Susumu, Alexandria, VA (US); Bing C. Mei, Philadelphia, PA (US); Hedi M Mattoussi, Alexandria, VA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 274 days.

(21) Appl. No.: 12/764,366

(22) Filed: Apr. 21, 2010

(65) Prior Publication Data

US 2010/0267967 A1    Oct. 21, 2010

Related U.S. Application Data

(60) Provisional application No. 61/171,203, filed on Apr. 21, 2009.

(51) Int. Cl.
*A61K 31/385* (2006.01)
*C07D 339/04* (2006.01)

(52) U.S. Cl. ......................................... 514/440; 549/39
(58) Field of Classification Search .................. 514/440; 549/39
See application file for complete search history.

(56) References Cited

U.S. PATENT DOCUMENTS

| | | | |
|---|---|---|---|
| 5,714,166 | A  | 2/1998 | Tomalia et al. |
| 6,426,513 | B1 | 7/2002 | Bawendi et al. |
| 6,444,143 | B2 | 9/2002 | Bawendi et al. |
| 6,756,354 | B2 | 6/2004 | Nelson |
| 7,160,613 | B2 | 1/2007 | Bawendi et al. |
| 7,198,847 | B2 | 4/2007 | Naasani |
| 7,361,516 | B2 | 4/2008 | Uyeda et al. |
| 7,648,843 | B2 | 1/2010 | Uyeda et al. |
| 2007/0298006 | A1 | 12/2007 | Tomalia et al. |

OTHER PUBLICATIONS

Gao et al., "Butylamide-terminated poly(amidoamine) dendritic gelators" Tetrahedron Letters 49 (2008) 6182-6187.
Gao et al., "Thermo- and pH-Responsive Dendronized Copolymers of Styrene and Maleic Anhydride Pendant with Poly(amidoamine) Dendrons as Side Groups" Macromolecules 2009, 42, 4273-4281.
Kim et al., "Oligomeric Ligands for Luminescent and Stable Nanocrystal Quantum Dots," J. Am. Chem. Soc. 125, 14652-14653 (2003).
Liu et al., "Compact Biocompatible Quantum Dots Functionalized for Cellular Imaging," J. Am. Chem. Soc. 130, 1274-1284 (2008).

(Continued)

Primary Examiner — Taofiq A Solola

(74) *Attorney, Agent, or Firm* — Amy L. Ressing; Joseph T. Grunkemeyer

(57) ABSTRACT

Disclosed herein are the compounds shown below and methods of their synthesis. The value m is a positive integer. R comprises an alkyl chain or an alkoxy chain. Each X comprises a metal binding group. Each E is a methoxy group or comprises a biomolecule reactive group or a residue thereof. E optionally comprises a protecting group. The value n is a positive integer. The value p is zero or one. Y is $OCH_3$, OH, $NH_2$, or COOH.

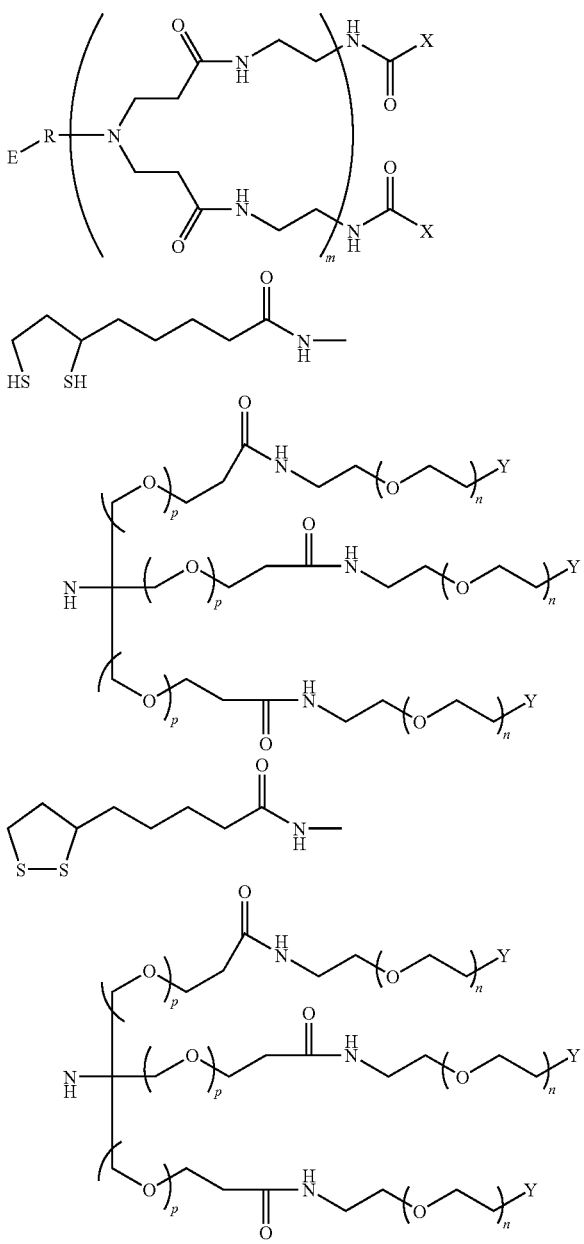

15 Claims, 5 Drawing Sheets

OTHER PUBLICATIONS

Mattoussi et al., "Self-Assembly of CdSe—ZnS Quantum Dot Bioconjugates Using an Engineered Recombinant Protein" J. Am. Chem. Soc. 2000, 122, 12142.

Mei et al., "Modular poly(ethylene glycol) ligands for biocompatible semiconductor and gold nanocrystals with extended pH and ionic stability" J. Mater. Chem. 2008, 18, 4949.

Susumu et al., "Enhancing the Stability and Biological Functionalities of Quantum Dots via Compact Multifunctional Ligands" J. Am. Chem. Soc.129, 13987-16996 (2007).

Uyeda et al., "Synthesis of Compact Multidentate Ligands to Prepare Stable Hydrophilic Quantum Dot Fluorophores" J. Am. Chem. Soc. 127, 3870-3878 (2005).

Search Report and Written Opinion in PCT/US2010/031868, (2010).

MULTIFUNCTIONAL METAL-CHELATING LIGANDS

This application claims the benefit of U.S. Provisional Application No. 61/171,203, filed on Apr. 21, 2010. The provisional application and all other publications and patent documents referred to throughout this nonprovisional application are incorporated herein by reference.

TECHNICAL FIELD

The present disclosure is generally related to metal-chelating ligands.

DESCRIPTION OF RELATED ART

The use of dihydrolipoic acid (DHLA), as a ligand to obtain water-soluble nanocrystals (via cap exchange) has been shown. Although DHLA-capped nanocrystals were stable and functional only in basic buffer solutions, the semiconductor quantum dots (QDs) aggregated in acidic solutions and under certain biological and coupling conditions (Mattoussi et al., *J. Am. Chem. Soc.* 2000, 122, 12142). This problem was addressed by appending poly(ethylene glycol) (PEG) segments to the acid group of the DHLA ligand to impart water solubility through solvent-PEG interactions (Uyeda et al., *J. Am. Chem. Soc.* 2005, 127, 3870). It has been shown that ligands containing 3 thiol groups bind more strongly to Au surfaces and Au nanoparticles (NPs) than ligands containing 1 or 2 thiol groups (DHLA binds through 2 thiols) (Li et al., *Nucleic Acids Res.* 2002, 30, 1558; Park et al., *Langmuir* 2005, 21, 2902; Zhang et al., *J. Am. Chem. Soc.* 2008, 130, 113; Srisombat et al., *Langmuir* 2008, 24, 7750).

Several examples exist of using multidentate ligands for preparing nanocrystals. However, each system has drawbacks. Phosphine-oligomers for stabilizing nanocrystals have been synthesized (Kim et al., *J. Am. Chem. Soc.* 2003, 125, 14652). This system relies on the oligomerization of trishydroxypropylphosphine, which lacks control and results in a mixture of oligomers including trimers, tetramers, pentamers, and hexamers. Furthermore, the resulting nanocrystals are only soluble in basic solution when the oligomers are functionalized with carboxyl groups, similar to the problem with pure DHLA.

A multidentate polymer has been reported that wraps to the surface of nanocrystals (Smith et al., *J. Am. Chem. Soc.* 2008, 130, 11278). However, this multidentate polymer does not allow good control over the distance of appended functional groups to the surface of the nanocrystal, which is important for sensing applications. Furthermore, cap exchange with the multidentate polymer requires a pre-cap exchange with thioglycerol. The quantum yield and polydispersity index of the resulting nanocrystals are highly dependent on the molar capping ratio. An optimal capping ratio can be determined, but is size dependent. Therefore, a new polymer must be synthesized for each nanocrystal for optimal performance. An amphiphilic multidentate ligand for preparing water-soluble quantum dots has been reported. The amphiphilic ligand forms an interdigitating bilayer on the surface of the QD, similar to a micelle, and obtains water-solubility via carboxyl groups (Kairdolf et al., *J. Am. Chem. Soc.* 2008, 130, 12866).

Other polymers have also been used, but the increased hydrodynamic radius of the nanocrystals limits their compatibility for biological applications. In comparison, cap exchange promises to provide compact nanocrystals.

BRIEF SUMMARY

Disclosed herein is a compound comprising the formula in Eq. (1). The value m is a positive integer. R comprises an alkyl chain, an oxyalkyl chain, or a polymer chain. Each X comprises a metal binding group. Each E is a methoxy group or comprises a biomolecule reactive group or a residue thereof. E optionally comprises a protecting group.

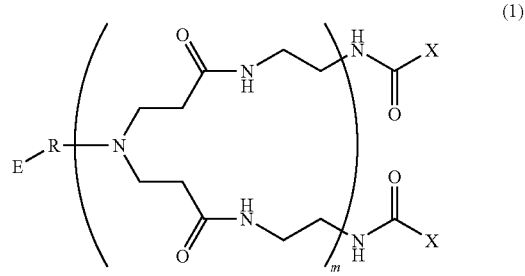

(1)

Also disclosed herein is a method comprising: reacting an alkyl- or oxyalkylamine comprising a methoxy group or a biomolecule reactive group or residue thereof and optionally a protecting group with methylacrylate to form a first intermediate; reacting the first intermediate with ethylenediamine to form a second intermediate; optionally repeating the reactions with methylacrylate and ethylenediamine one or more times to form a dendrimer; and reacting the second intermediate or the dendrimer with a carboxylic acid comprising a metal binding group to form a compound comprising the formula in Eq. (1).

Also disclosed herein is a compound comprising a formula in Eq. (2). The value n is a positive integer. The value p is zero or one. Y is $OCH_3$, OH, $NH_2$, or COOH.

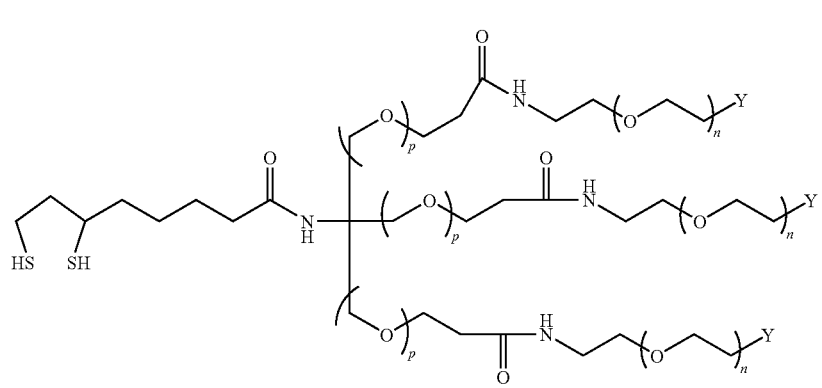

(2)

-continued

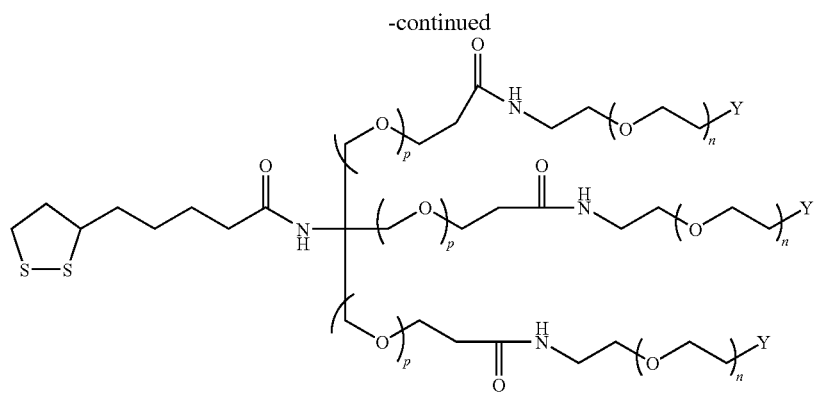

BRIEF DESCRIPTION OF THE DRAWINGS

A more complete appreciation of the invention will be readily obtained by reference to the following Description of the Example Embodiments and the accompanying drawings.

DETAILED DESCRIPTION OF EXAMPLE EMBODIMENTS

Figure 1:
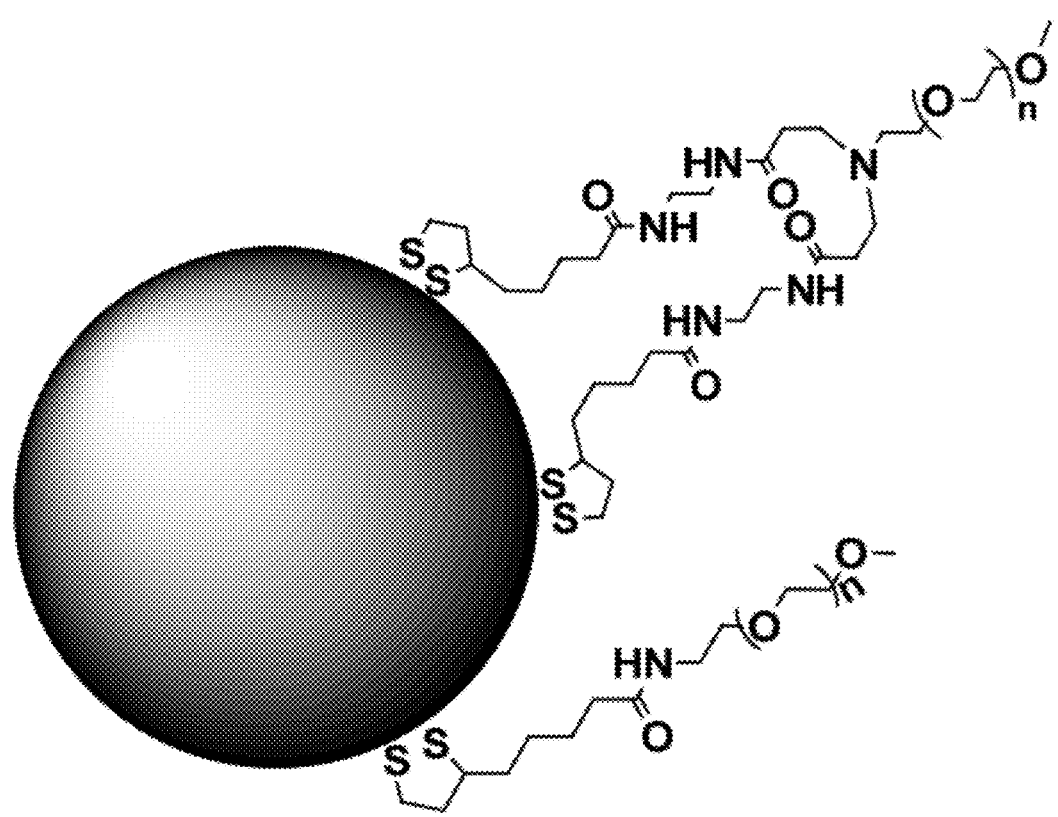
FIG. 1 shows mixed surface ligands yielding water-soluble nanocrystals.

In the following description, for purposes of explanation and not limitation, specific details are set forth in order to provide a thorough understanding of the present disclosure. However, it will be apparent to one skilled in the art that the present subject matter may be practiced in other embodiments that depart from these specific details. In other instances, detailed descriptions of well-known methods and devices are omitted so as to not obscure the present disclosure with unnecessary detail.

Described herein is the synthesis of a chelating, multidentate organic ligand and its use for capping the surface of semiconductor and metal nanocrystals (including core and core/shell materials), yielding them highly stable and water-soluble. The organic ligands are modular in structure, and each is composed of two, four, or more coordinating (or chelating) groups for strong anchoring onto the nanocrystal surface and a poly(ethylene glycol) segment of varying lengths to impart solubility in water. The other end of the poly(ethylene glycol) segment can be modified with, for example, amino, carboxylic acid, alkynes, and other functionalities that allow further conjugation and reactivity (including conjugation to bio-molecules). Control over the surface reactivity of the final nanoparticle can be achieved by using a mixture of end-functionalized and un-functionalized (inert) ligands. The newly functionalized nanocrystals can be conjugated with more than one target molecule to prepare highly ordered structures for a variety of applications. The chelating (multidentate) group may strongly anchor the organic ligands to the surface of the nanocrystal, which enhances the stability of the nanocrystals (unlike single thiol or single phosphine-based ligands that are weakly bound to the surface and dissociate). The enhanced binding-nature of the multidentate ligand may also make it useful for anchoring target molecules to the surface of nanocrystals.

In the first step of the synthesis, an alkyl- or oxyalkylamine is reacted with methylacrylate to form a first intermediate. This step is shown in Eq. (3). Two methylacrylates react with the amine. The amine comprises a methoxy group ($CH_3O$—) or a biomolecule reactive group. Suitable biomolecule reactive groups include, but are not limited to, $NH_2$—, HOOC—, HO—, azide, biotin, an alkynyl group, or an aryl group. One example of the amine is $CH_3$—O—$(CH_2$—$CH_2$—$O)_n$—$CH_2$—$CH_2$—$NH_2$, where n is a positive integer and may be, but is not limited to, 1 to 50. A structure where E is biotin is shown in Eq. (4).

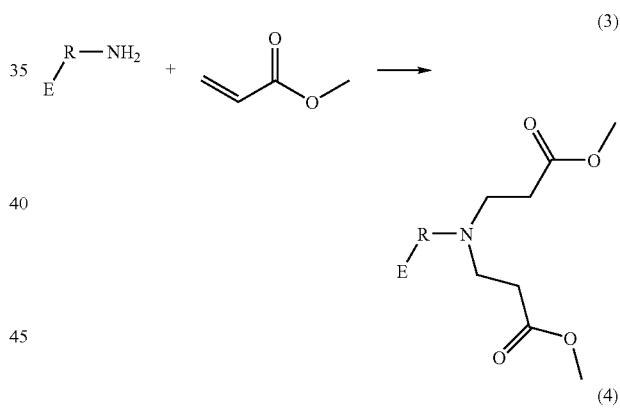

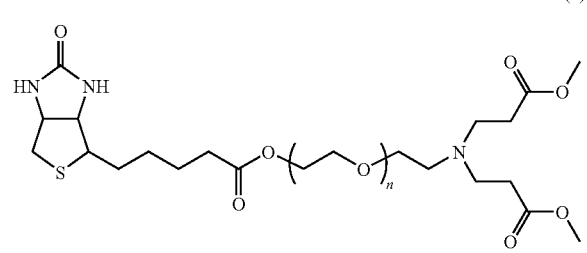

E may also be a residue of the biomolecule reactive group when this group is reacted with a protecting group. For example, a $NH_2$— biomolecule reactive group may be a residue of the form —NH—. A variety of such protecting groups suitable for reacting with the biomolecule reactive groups are known in the art.

In the next step of the synthesis, the first intermediate is reacted with ethylenediamine to form a second intermediate. This step is shown in Eq. (5). An amine reacts with each of the COOCH₃ groups produced in the previous step, leaving a primary amine at the end of each branch.

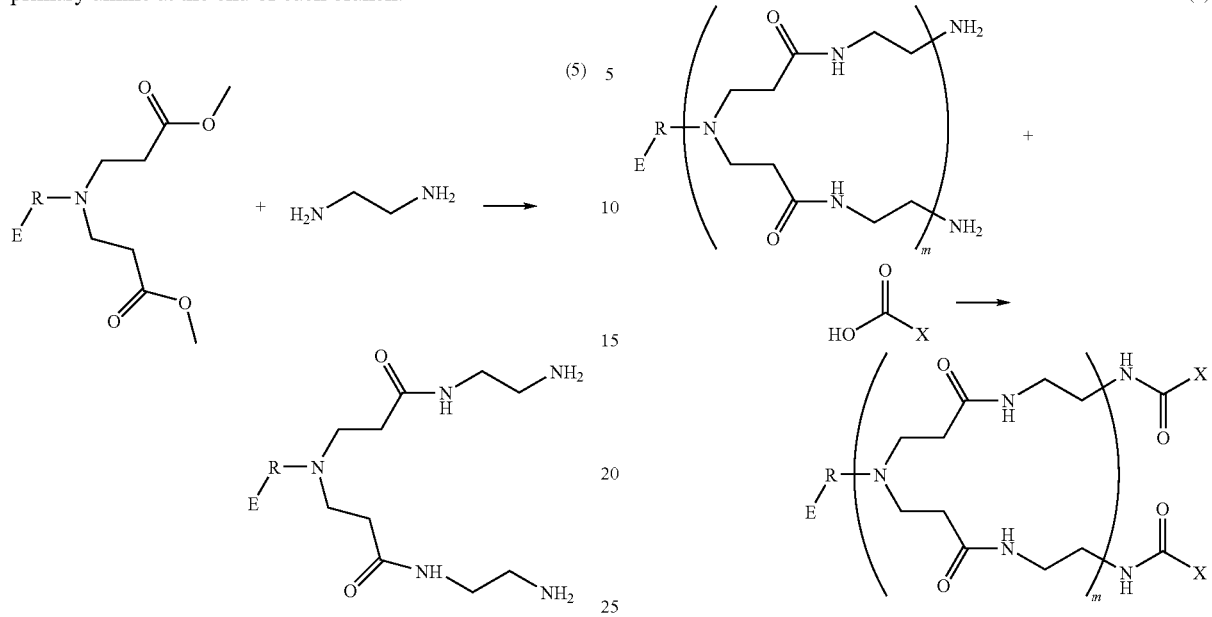

(5)

Optionally, the above two steps are repeated one or more times to form a dendrimer. This is shown in Eq. (6). Each reaction with methylacrylate doubles the number of branches. Each reaction with ethylenediamine produces primary amines for repeating the cycle. There is no limit to the number of cycles or generations that may be performed. Where m is 2, the cycle is repeated twice. Where m is 1, there is no repetition.

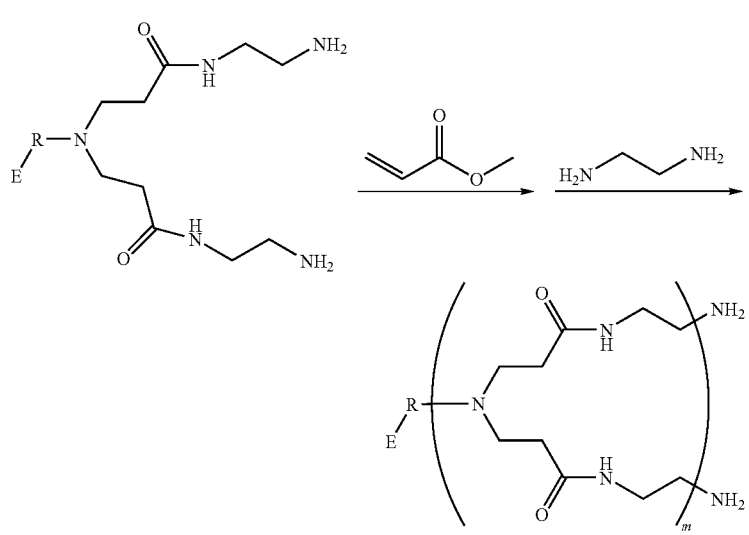

(6)

In the next step, the second intermediate or the dendrimer is reacted with a carboxylic acid comprising a metal binding group. This step is shown in Eq. (7). A suitable carboxylic acid is thioctic acid, which produces a ligand having two or more 5-membered disulfide rings. In an optional step, the disulfide rings are reacted with sodium borohydride to produce a dithiol group.

Both the disulfide ring and the dithiol group may react with a gold or metal nanoparticle. The dithiol may also react with a semiconductor quantum dot. Suitable quantum dot materials include, but are not limited to, comprises a cadmium binary compound, a indium binary compound, a lead binary compound, a zinc binary compound, cadmium sulfide (CdS), cadmium selenide (CdSe), cadmium telluride (CdTe), indium phosphide (InP), indium arsenide (InAs), zinc sulfide (ZnS), zinc selenide (ZnSe), zinc telluride (ZnTe), lead selenide (PbSe), and lead sulfide (PbS). The quantum dot may also have a core-shell structure, where each component comprises a different material.

Obtaining water-soluble nanocrystals prepared by cap-exchange is not limited to using exclusively the chelating PEG ligand. Mixtures of thiol containing ligands can be used in conjunction with the tetradentate-chelating PEG ligand to prepare water-soluble nanocrystals (FIG. 1). For example, DHLA, DHLA-PEG-Y (Y=NH$_2$, COOH, biotin, azide, alkyne, OH, OCH$_3$), and single thiol containing species can be used to prepare a QD with a mixture of capping ligands for imparting multiple functionality to one QD.

In another optional step, any protecting group is removed by methods known in the art.

The disclosed ligands may be of interest in nano-biotechnology and the emerging field of nanomedicine. This is due to the unique properties of luminescent quantum dots (e.g., high quantum yield, chemical stability, and tunable absorption and emission wavelengths) and Au nanoparticles. Very stable hydrophilic nanoparticles and their conjugates in a variety of biological conditions (broad pH range and excess ions) may be produced. It is also compatible with commonly used bioconjugation strategies such as avidin-biotin binding and zero cross linking with 1-ethyl-3-(3-dimethylaminopropyl)carbodiimide hydrochloride (EDAC or EDC).

In addition to the PEG segment which confers water-solubility to the nanocrystal and an end group that offers further conjugation and reactivity, the present ligand design may provide a very strong anchoring group (4 thiols) and promote tight binding to the nanocrystal surface. This ligand design is not limited to 2 DHLA groups. Formation of a dendrimer as described above allows one to make a ligand with multiple DHLA groups. This can be achieved by taking intermediate B from FIG. 2 and repeating steps 1-2 iteratively to yield a branched structure with multiple NH$_2$ groups (compound E) for attaching thioctic acid groups, which can then be reduced to DHLA, compound F (FIG. 3). Compound F is a multidentate ligand that can bind through 8 thiol groups.

Figure 4:
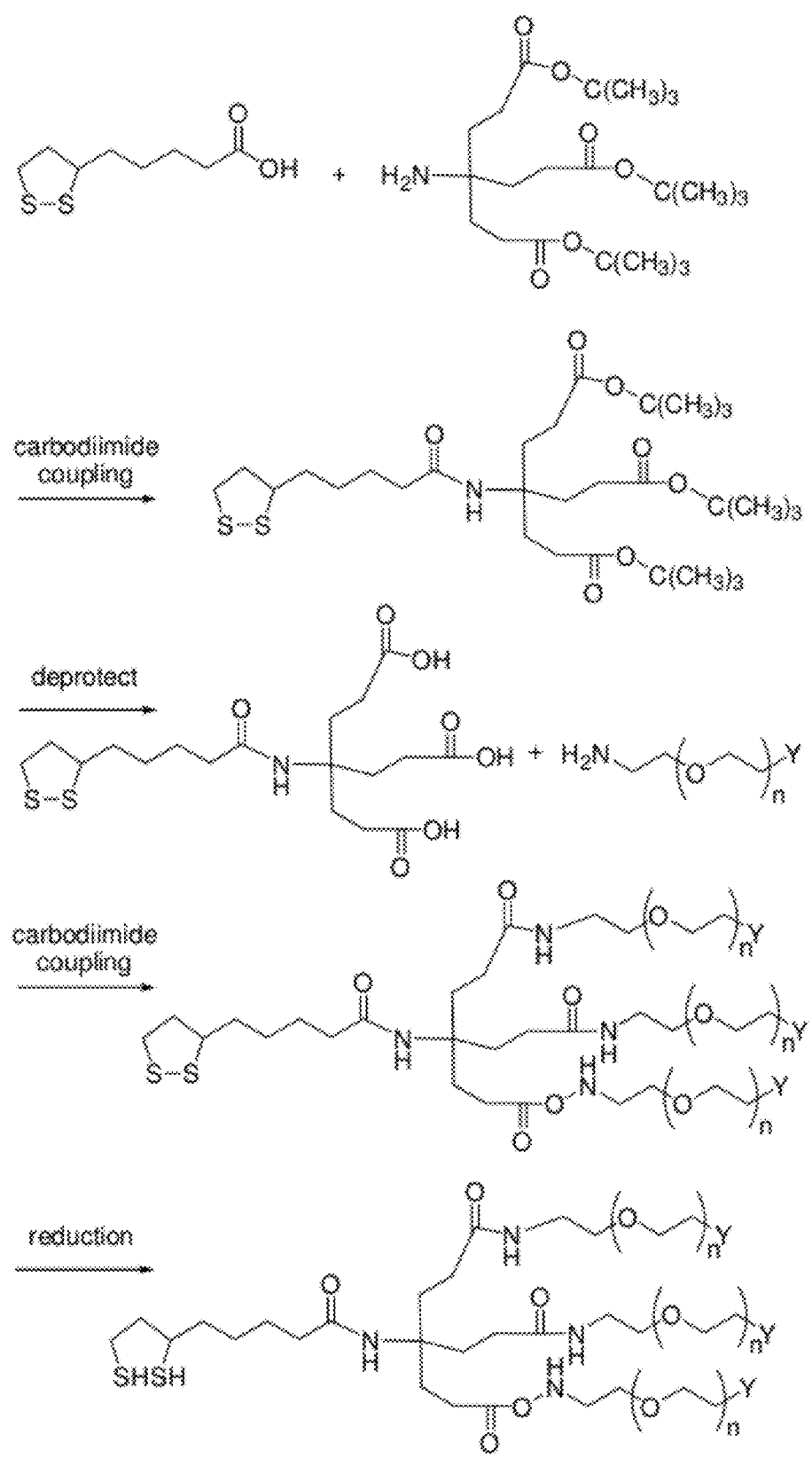
FIGS. 4 and 5 show proposed syntheses of compounds of Eq. (2).
Figure 5:
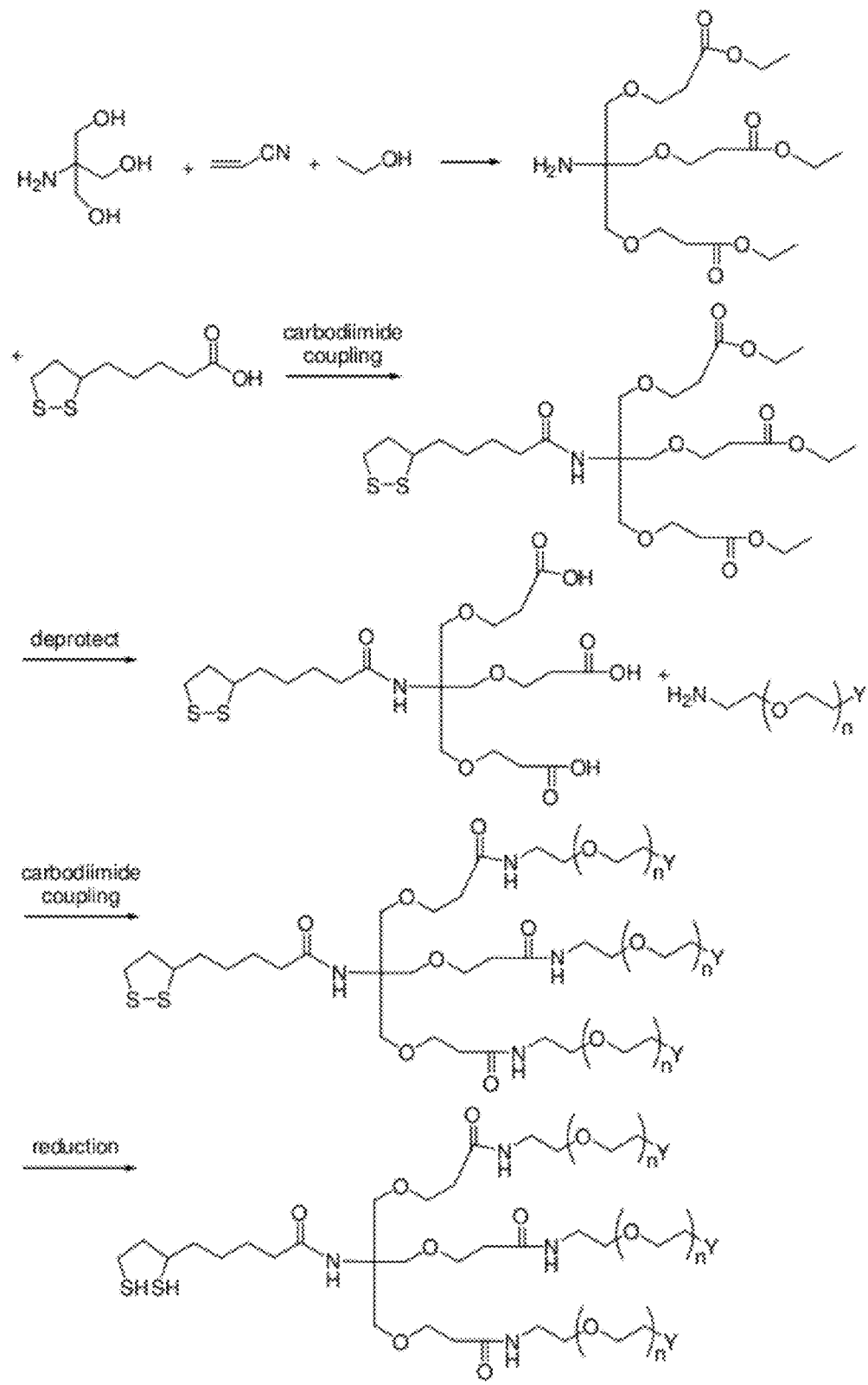

Also disclosed herein is a complimentary ligand for preparing highly stable water-soluble nanocrystals by diminishing the number of chelating groups and increasing the number of PEG moieties (Eq. (2)). This ligand binds to the surface of nanocrystals through the DHLA group (or TA if, for example, it is used on Au nanoparticles). The PEG groups can be functionalized with any combination of end groups Y that include, but are not limited to, OCH$_3$, OH, NH$_2$, and COOH, which will provide a multifunctional surface on the nanocrystal. FIGS. 4 and 5 show proposed syntheses of these compounds.

The following examples are given to illustrate specific applications. These specific examples are not intended to limit the scope of the disclosure in this application.

EXAMPLE 1

Figure 2:
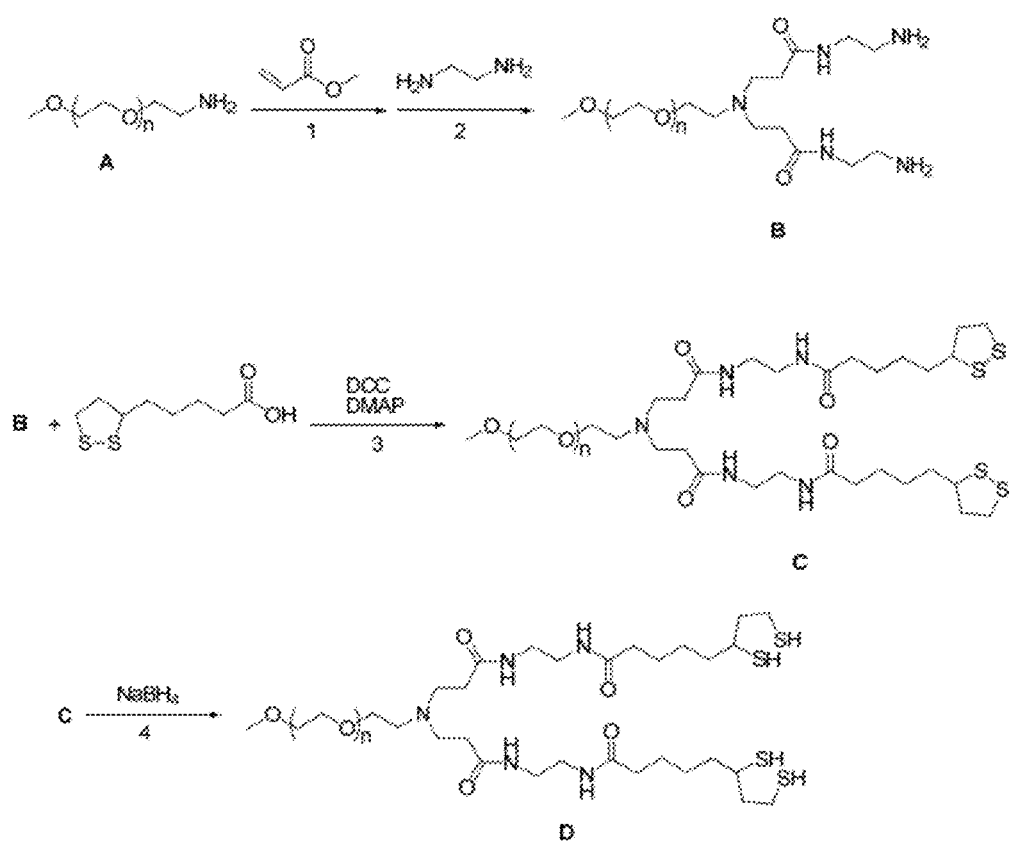
FIG. 2 shows a synthetic scheme for a tetradentate-chelating ligand.
Figure 3:
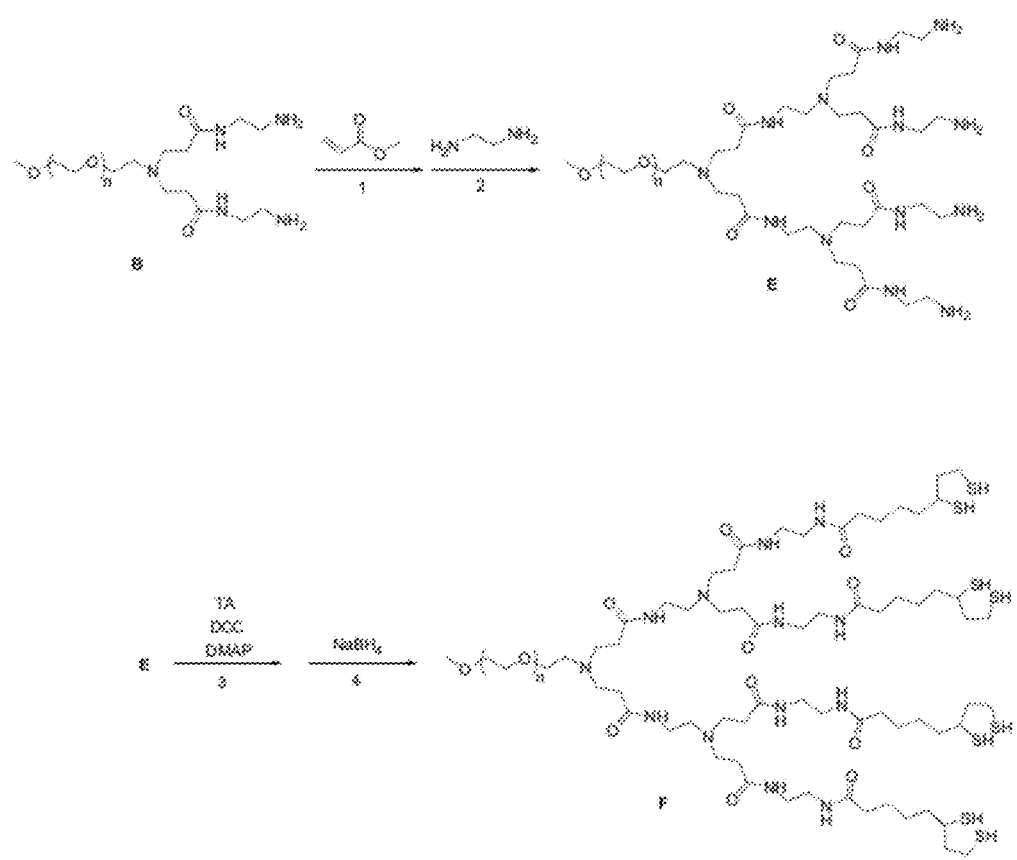
FIG. 3 shows dendrimer-like synthesis to create a multidentate ligand.

Preparation of bis(DHLA)-PEG-OCH$_3$— The preparation of the tetradentate-chelating PEGylated ligand, bis(DHLA)-PEG-OCH$_3$ (D), is shown in FIG. 2. In a typical synthesis, the OH group of commercially available poly(ethylene glycol) methyl ether was converted to an amine (compound A) using a procedure reported previously (Mei et al., *J. Mater. Chem.* 2008, 18, 4949). Alkylation of the amine with methyl acrylate via Michael addition, followed by amidation with excess ethylenediamine yielded a branched structure with two amine groups per PEG molecule, bis(NH$_2$)-PEG-OCH$_3$ (B). This two-step process is often used in dendrimer synthesis to yield branched structures (Matthews et al., *Prog. Polym. Sci.* 1998, 23, 1; Tomalia et al., *Macromolecules* 1986, 19, 2466). The amine groups were then coupled to commercially available thioctic acid (TA) in the presence of N,N'-dicyclohexylcarbodiimide (DCC) and 4-(dimethylamino)pyridine (DMAP) and then purified by column chromatography using chloroform and methanol to yield bis(TA)-PEG-OCH$_3$ (C). The resulting ligand can be used for capping Au NPs without further manipulation. For QDs, however, reduction of the dithiolane ring(s) to produce thiol groups was required for coordination on the semiconducting surface. The ring-opening was carried out in the presence of sodium borohydride to yield bis(DHLA)-PEG-OCH$_3$ (D), a tetradentate-chelating ligand. Characterization of the final product and intermediates was achieved using $^1$H NMR spectroscopy. In particular, the presence of two DHLA groups per ligand molecule was confirmed by integration of the $^1$H NMR spectrum.

EXAMPLE 2

Quantum dots—Water-soluble semiconductor quantum dots were prepared by exchanging the native hydrophobic organic capping shell of trioctylphosphine/trioctylphosphine oxide (TOP/TOPO) with the hydrophilic chelating PEG ligand of Example 1. First, a small volume of TOP/TOPO QDs were precipitated with ethanol and centrifuged to remove excess TOP/TOPO. An excess of the chelating PEG ligand (~50,000 equivalents/QD) was added to the precipitated QDs and the system was evacuated and placed under an atmosphere of nitrogen. Ethanol was added and the mixture was stirred at 60° C. overnight, resulting in a homogenous solution. The QDs were then precipitated with a mixture of ethanol, chloroform, and hexanes. The precipitated QDs were dissolved in water, filtered through a 0.45 μm PTFE frit, and then filtered 2-3 times using a centrifuge filter device with a nominal molecular weight cut-off of 50K. Quantum yields for QDs with the chelating PEG ligands were comparable to those made from a PEG ligand with only one DHLA group.

Obviously, many modifications and variations are possible in light of the above teachings. It is therefore to be understood that the claimed subject matter may be practiced otherwise than as specifically described. Any reference to claim elements in the singular, e.g., using the articles "a," "an," "the," or "said" is not construed as limiting the element to the singular.

What is claimed is:
1. A compound comprising the formula:

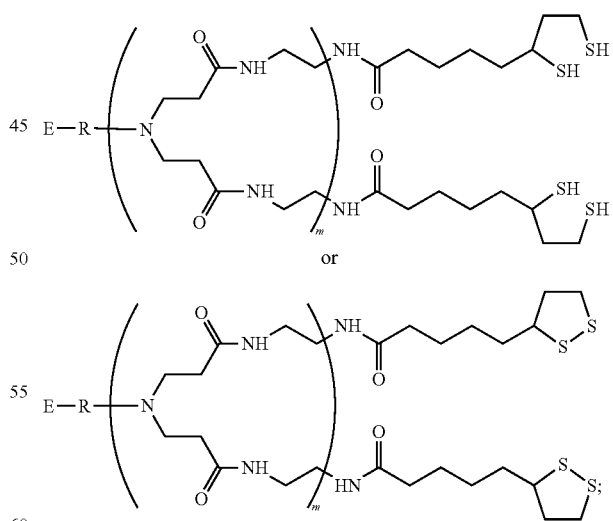

wherein R comprises an alkyl chain or a poly(ethylene glycol) chain;
wherein m is a positive integer; and
wherein E is CH$_3$O—, H$_2$N—, HOOC—, HO—, azide, biotin, an alkynyl group, or an aryl group and optionally comprises a protecting group.

2. The compound of claim 1, wherein the compound comprises the formula:
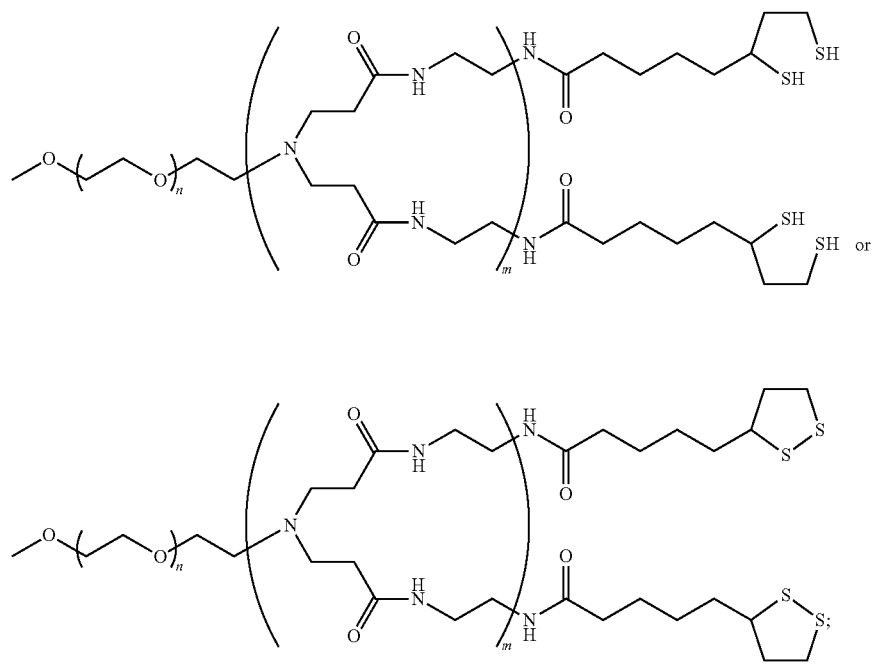
wherein n is from 1 to 50.
3. The compound of claim 2, wherein m is 1 and the compound is
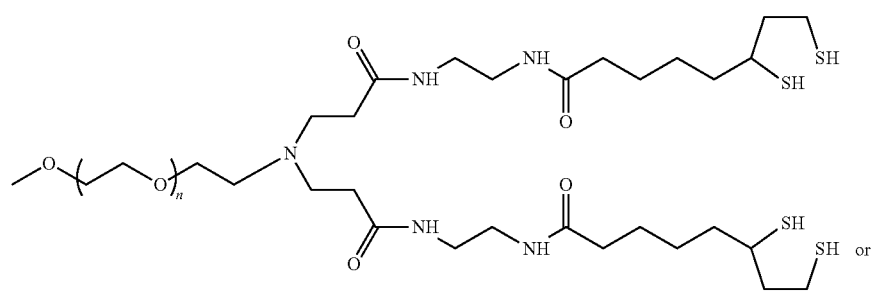
4. The compound of claim 2, wherein m is 2 and the compound is

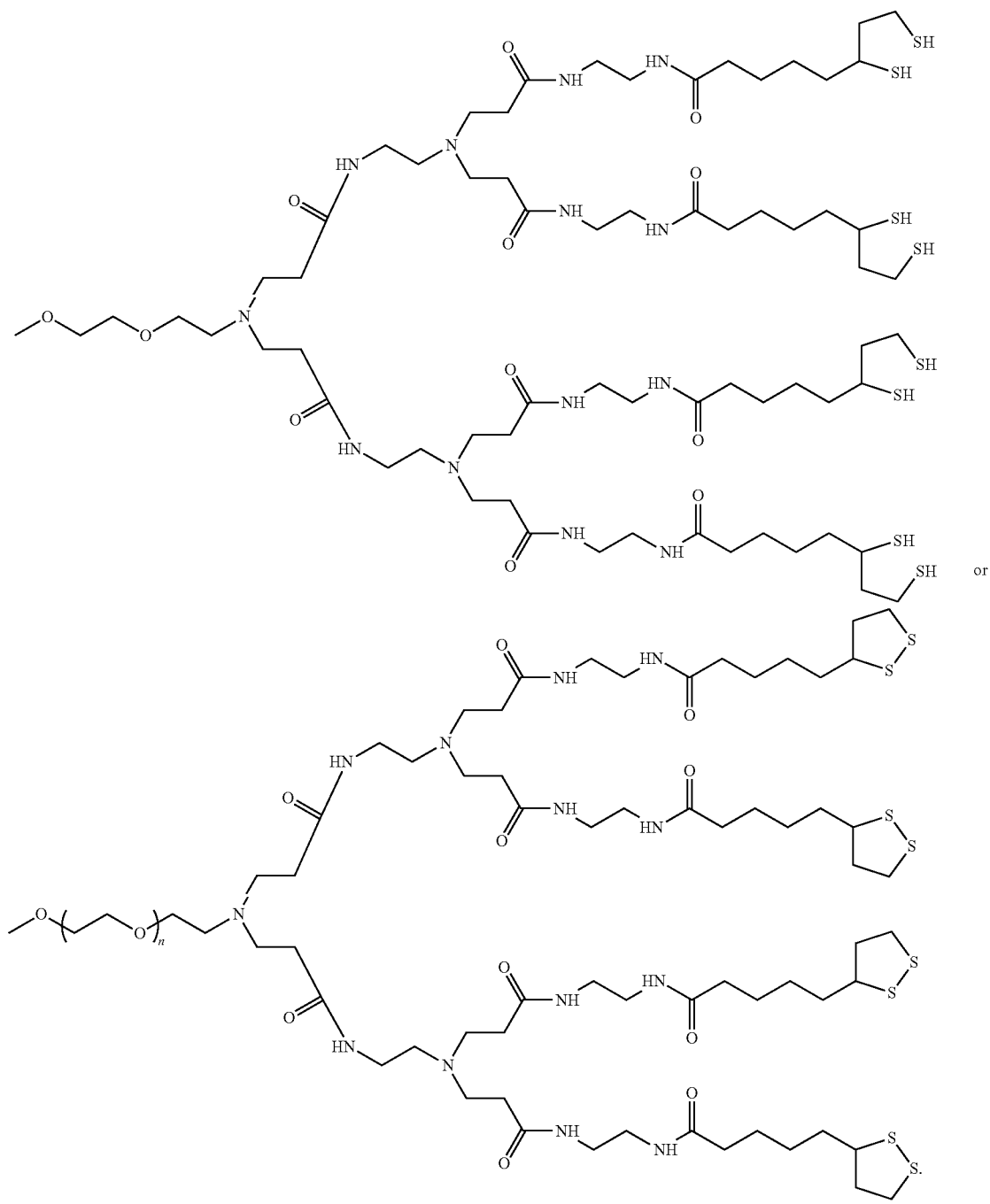

5. A composition comprising:
a semiconductive quantum dot comprising a cadmium binary compound, a indium binary compound, a lead binary compound, a zinc binary compound, cadmium sulfide, cadmium selenide, cadmium telluride, indium phosphide, indium arsenide, zinc sulfide, zinc selenide, zinc telluride, lead selenide, or lead sulfide or a metal nanoparticle; and
the compound of claim 1 bound to the surface of the quantum dot or nanoparticle.

6. A method comprising:
reacting an alkyl- or poly(ethylene glycol)amine comprising $CH_3O-$, $H_2N-$, $HOOC-$, $HO-$, azide, biotin, an alkynyl group, or an aryl group and optionally a protecting group with methylacrylate to form a first intermediate;

reacting the first intermediate with ethylenediamine to form a second intermediate;

optionally repeating the reactions with methylacrylate and ethylenediamine one or more times to form a dendrimer; and reacting the second intermediate or the dendrimer with thioctic acid to form a compound comprising the formula:

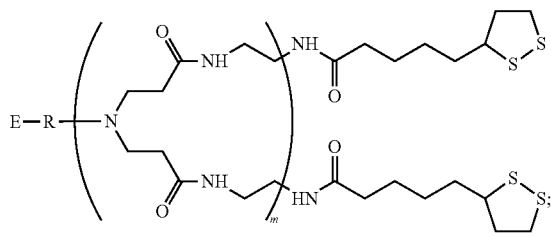

wherein m is a positive integer;
wherein R comprises the alkyl chain or the poly(ethylene glycol) chain; and
wherein E is CH$_3$O—, H$_2$N—, HOOC—, HO—, azide, biotin, an alkynyl group, or an aryl group and optionally comprises a protecting group.

7. The method of claim 6, further comprising:
removing the protecting group.

8. The method of claim 6;
wherein the poly(ethylene glycol)amine is CH$_3$—O—(CH$_2$—CH$_2$—O)$_n$—CH$_2$—CH$_2$—NH$_2$;
wherein n is from 1 to 50, forming the compound:

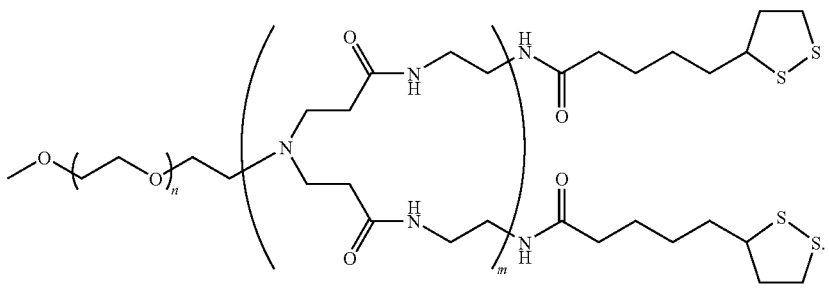

9. The method of claim 8, further comprising:

reacting the product of reacting with thioctic acid with a metal nanoparticle.

10. The method of claim 8, further comprising:

reacting the product of reacting with thioctic acid with sodium borohydride to form the compound:

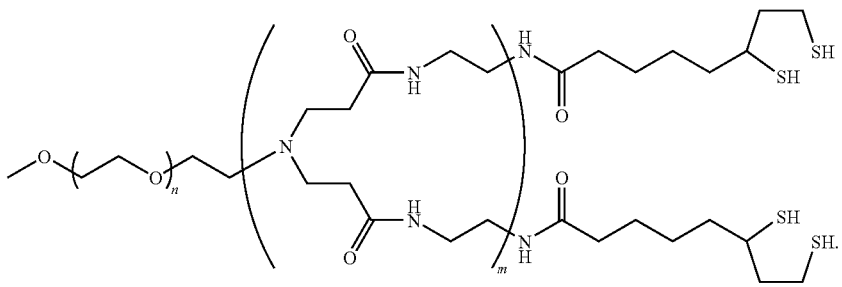

11. The method of claim 10, further comprising:
reacting the product of reacting with sodium borohydride with a semiconductive quantum dot comprising a cadmium binary compound, a indium binary compound, a lead binary compound, a zinc binary compound, cadmium sulfide, cadmium selenide, cadmium telluride, indium phosphide, indium arsenide, zinc sulfide, zinc selenide, zinc telluride, lead selenide, or lead sulfide or a metal nanoparticle.

12. A compound comprising the formula:

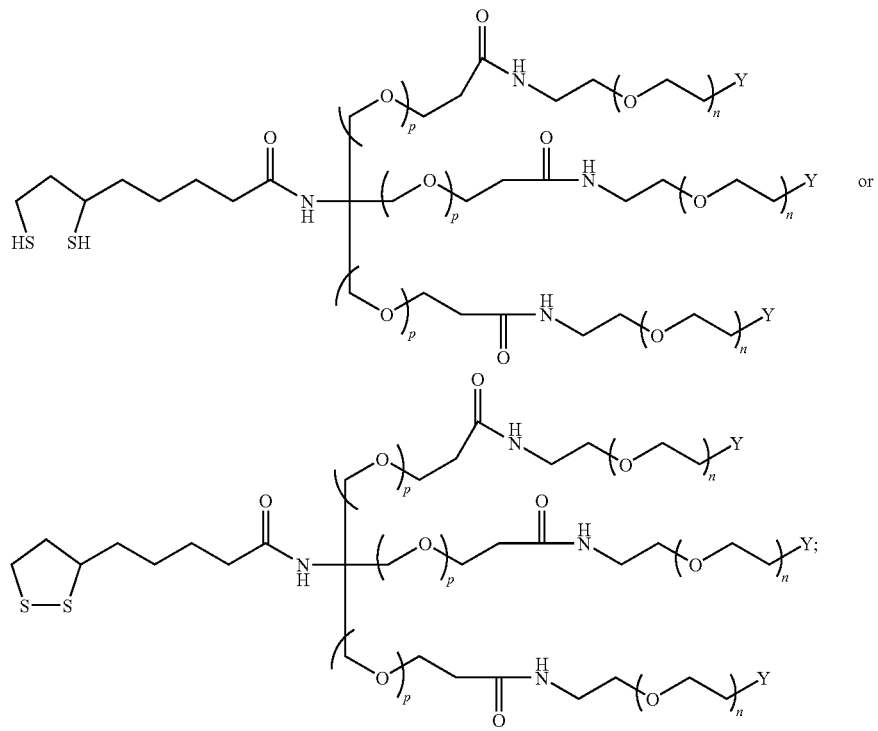

wherein n is from 1 to 50;
wherein p is zero or one; and
wherein Y is $OCH_3$, OH, $NH_2$, or COOH.

13. The compound of claim 12, wherein p is 0.

14. The compound of claim 12, wherein p is 1.

15. A composition comprising:
a semiconductive quantum dot comprising a cadmium binary compound, a indium binary compound, a lead binary compound, a zinc binary compound, cadmium sulfide, cadmium selenide, cadmium telluride, indium phosphide, indium arsenide, zinc sulfide, zinc selenide, zinc telluride, lead selenide, or lead sulfide or a metal nanoparticle; and
the compound of claim 12 bound to the surface of the quantum dot or nanoparticle.

* * * * *